US011229703B2

(12) United States Patent
Kelly

(10) Patent No.: US 11,229,703 B2
(45) Date of Patent: Jan. 25, 2022

(54) RADIOTHERAPY IMPROVEMENTS

(71) Applicant: NOXOPHARM LIMITED, Turramurra (AU)

(72) Inventor: Graham Kelly, Turramurra (AU)

(73) Assignee: NOXOPHARM LIMITED, Turramurra (AU)

( * ) Notice: Subject to any disclaimer, the term of this patent is extended or adjusted under 35 U.S.C. 154(b) by 0 days.

(21) Appl. No.: 16/091,706

(22) PCT Filed: Apr. 6, 2017

(86) PCT No.: PCT/AU2017/050299
§ 371 (c)(1),
(2) Date: Oct. 5, 2018

(87) PCT Pub. No.: WO2017/173496
PCT Pub. Date: Oct. 12, 2017

(65) Prior Publication Data
US 2019/0262451 A1    Aug. 29, 2019

Related U.S. Application Data

(60) Provisional application No. 62/461,559, filed on Feb. 21, 2017, provisional application No. 62/318,946, filed on Apr. 6, 2016.

(30) Foreign Application Priority Data

Jul. 28, 2016 (WO) ................ PCT/AU2016/050674

(51) Int. Cl.
| *A61K 41/00* | (2020.01) |
| *A61P 35/04* | (2006.01) |
| *A61K 31/352* | (2006.01) |
| *A61K 31/353* | (2006.01) |
| *A61K 31/435* | (2006.01) |
| *A61K 31/382* | (2006.01) |
| *A61K 31/366* | (2006.01) |

(52) U.S. Cl.
CPC ........ *A61K 41/0038* (2013.01); *A61K 31/352* (2013.01); *A61K 31/353* (2013.01); *A61K 31/366* (2013.01); *A61K 31/382* (2013.01); *A61K 31/435* (2013.01); *A61P 35/04* (2018.01)

(58) Field of Classification Search
CPC ............. A61K 41/0038; A61K 31/352; A61K 31/353; A61K 31/366; A61K 31/382; A61K 31/435; A61P 35/04
See application file for complete search history.

(56) References Cited

U.S. PATENT DOCUMENTS

| 7,488,494 | B2 * | 2/2009 | Heaton | C07D 311/26 424/439 |
| 8,084,628 | B2 * | 12/2011 | Heaton | A61K 31/353 549/403 |
| 8,163,795 | B2 * | 4/2012 | Heaton | A61K 31/337 514/457 |
| 8,461,361 | B2 * | 6/2013 | Heaton | A61K 33/243 549/399 |
| 8,697,891 | B2 * | 4/2014 | Heaton | A61K 31/353 549/403 |
| 8,957,109 | B2 * | 2/2015 | Heaton | A61K 31/337 514/457 |
| 9,138,478 | B2 * | 9/2015 | Heaton | C07D 311/38 |
| 9,198,895 | B2 * | 12/2015 | Heaton | A61K 31/337 |
| 9,381,186 | B2 * | 7/2016 | Heaton | A61K 31/353 |
| 2004/0152761 | A1 * | 8/2004 | Heaton | C07D 311/58 514/456 |
| 2005/0049424 | A1 * | 3/2005 | Kelly | A61K 31/12 549/234 |
| 2005/0154452 | A1 | 7/2005 | Hezi-Yamit et al. | |
| 2006/0074127 | A1 * | 4/2006 | Heaton | A61P 35/00 514/456 |
| 2006/0100238 | A1 * | 5/2006 | Kelly | C07D 311/68 514/312 |
| 2006/0167037 | A1 * | 7/2006 | Kelly | A61K 31/192 514/296 |
| 2006/0183728 | A1 * | 8/2006 | Kelly | A61K 31/555 514/184 |
| 2007/0036834 | A1 | 2/2007 | Pauletti et al. | |
| 2007/0196381 | A1 | 8/2007 | Holt | |
| 2009/0028964 | A1 | 1/2009 | Muni et al. | |
| 2009/0104235 | A1 | 4/2009 | Heinrich | |
| 2009/0233999 | A1 * | 9/2009 | Heaton | C07C 45/46 514/456 |
| 2010/0152284 | A1 | 6/2010 | Brown et al. | |

(Continued)

FOREIGN PATENT DOCUMENTS

| WO | WO-9808503 A1 * | 3/1998 | ........ A61K 31/353 |
| WO | WO 2000/066576 | 11/2000 | |

(Continued)

OTHER PUBLICATIONS

O. Yossepowitch et al., 53 European Urology, 950-959 (2008) (Year: 2008).*
M. Lock et al., 7 Cureus, 2-10 (2015) (Year: 2015).*
Y. Cho et al., Plos One, 1-12 (Jan. 25, 2016) (Year: 2016).*
M. Postow et al., 366 The New England Journal of Medicine, 925-931 (2012) (Year: 2012).*
K. Reynders et al., 41 Cancer Treatment Reviews, 503-510 (2015) (Year: 2015).*
A. Alvero et al., Future Oncol., 475-482 (2008) (Year: 2008).*
M. Aguero et al., 70 The Prostate, 1211-1221 (2010) (Year: 2010).*
S. Mahoney et al., 37 J. Biosci., 73-84 (2012) (Year: 2012).*
E. Yaykaci et al., 19 EXCLI Journal, 936-949 (2020) (Year: 2020).*
H. Bartelink et al., 38 European Journal of Cancer, 216-222 (2002) (Year: 2002).*
Gruca et al., "Synthetic genistein glycosides inhibiting EGFR phosphorylation enhance the effect of radiation in HCT 116 colon cancer cells," *Molecules*, 19(11):18558-18573, 2014.

(Continued)

*Primary Examiner* — Alexander R Pagano
(74) *Attorney, Agent, or Firm* — Parker Highlander PLLC

(57) ABSTRACT

A method for inducing abscopal, complete or partial response to radiotherapy comprising administering isoflavone compounds and irradiating with a cytotoxic dose of ionising radiation so that fewer than all of the plurality of tumours are irradiated.

21 Claims, No Drawings

(56) References Cited

U.S. PATENT DOCUMENTS

| | | | | |
|---|---|---|---|---|
| 2011/0166142 | A1* | 7/2011 | Eiffe | A61P 1/04 514/242 |
| 2012/0039917 | A1 | 2/2012 | Husband et al. | |
| 2016/0340329 | A1* | 11/2016 | Heaton | C07D 407/10 |
| 2019/0117618 | A1* | 4/2019 | Kelly | A61K 9/02 |
| 2019/0117620 | A1* | 4/2019 | Kelly | A61K 9/0034 |
| 2019/0160004 | A1* | 5/2019 | Kelly | A61K 9/0031 |

FOREIGN PATENT DOCUMENTS

| | | | | |
|---|---|---|---|---|
| WO | WO 2003/035635 | | 5/2003 | |
| WO | WO 2003/086386 | | 10/2003 | |
| WO | WO 2004/009035 | | 1/2004 | |
| WO | WO-2004030662 | A1 * | 4/2004 | A61K 31/12 |
| WO | WO-2005027842 | A2 * | 3/2005 | A61K 45/06 |
| WO | WO 2005/049008 | | 6/2005 | |
| WO | WO-2005049008 | A1 * | 6/2005 | A61K 2300/00 |
| WO | WO 2006/032086 | | 3/2006 | |
| WO | WO 2006/108212 | | 10/2006 | |
| WO | WO 2007/035515 | | 3/2007 | |
| WO | WO 2009/003229 | | 1/2009 | |
| WO | WO 2010/022467 | | 3/2010 | |
| WO | WO 2010/054438 | | 5/2010 | |
| WO | WO 2011/121418 | | 10/2011 | |
| WO | WO-2013056217 | A1 * | 4/2013 | A61K 31/711 |
| WO | WO-2014160130 | A1 * | 10/2014 | A61K 2300/00 |
| WO | WO 2015/069562 | | 5/2015 | |
| WO | WO 2017/025918 | | 2/2017 | |
| WO | WO-2017079746 | A2 * | 5/2017 | C07K 16/2818 |
| WO | WO 2017/173498 | | 10/2017 | |
| WO | WO 2017/181242 | | 10/2017 | |
| WO | WO 2019/240871 | | 12/2019 | |
| WO | WO 2019/240872 | | 12/2019 | |
| WO | WO 2020/051644 | | 3/2020 | |

OTHER PUBLICATIONS

Kim et al., "Genistein decreases cellular redox potential, partially suppresses cell growth in HL-60 leukemia cells and sensitizes cells to γ-radiation-induced cell death," *Molecular Medicine Reports*, 10(6):2786-2792, 2014.

Ludgate, "Optimizing cancer treatments to induce an acute immune response: radiation Abscopal effects, PAMPs, and DAMPs," *Clinical Cancer Research*, 18(17):4522-4525, 2012.

PCT International Search Report and Written Opinion issued in International Application No. PCT/AU2017/050299, dated May 24, 2017.

Raffoul et al., "Radiosensitization of prostate cancer by soy isoflavones," *Current Cancer Drug Targets*, 7(8) :759-765, 2007.

Royal North Shore Hospital, "Phase I Study of Idronoxil Combined With Radiation Treatment in Men With Metastatic Prostate Cancer," ClinicalTrials.gov archive [online], NCT03041285 on Feb. 1, 2017, retrieved from https://clinicaltrials.gov/archive/NCT03041285/2017_02_01 on May 2, 2017.

Shin et al., "Sensitization of the apoptotic effect of gamma-irradiation in genistein-pretreated CaSki cervical cancer cells," *Journal of Microbiology & Biotechnology*, 18(3):523-531, 2008.

Ahmad et al., "Perspectives on the Role of Isoflavones in Prostate Cancer", The AAPS Journal, vol. 15, No. 4, Jul. 4, 2013 (Jul. 4, 2013), pp. 991-1000, XP55626811, DOI: 10.1208/s12248-013-9507-1 pp. 994-995.

Ahmad et al., "Soy isoflavones in conjunction with radiation therapy in patients with prostate cancer," Nutrition and Cancer England 2010, Taylor & Francis, US, vol. 62, No. 7, Jan. 1, 2010 (Jan. 1, 2010), pp. 996-1000.

Anonymous, "Brain Cancer Study Commences," Feb. 1, 2017 (Feb. 1, 2017), pp. 1-3, XP55639769, Sydney, Australia Retrieved from the Internet: URL:https://www.noxopharm.com/site/PDF/1147O/BrainCancerStudyCommences [retrieved on Nov. 6, 2019].

Anonymous, "Idronoxil suppository NOX66", National Cancer Institute Drug Dictionary, XP009514254. Retrieved from the Internet <URL:https://www.cancer.gov/publications/dictionaries/cancer-drug/def/idronoxil-suppository-nox66> on May 2, 2017.

Baviskar et al., "Drug delivery on rectal absorption: Suppositories," International Journal of Pharmaceutical Sciences Review and Research, 21(1):70-76, 2013.

Cremer Health, "Witepsol," Retrieved on Sep. 27, 2019. Retrieved from the internet <URL: https://www.pharmacompass.com/pAssets/pdf/edqm/application/witepsol.pdf>; pp. 1-44. (Year: 2019).

Database WPI Week 201204 Thomson Scientific, London, GB; AN 2011-B25102 & KR 2011 0004525 A (Univ Dong EUI IND Academic Coop Found), © WPI / 2017 Clarivate Analytics.

Howes et al., "Pharmacokinetic of phenoxodiol, a novel isoflavone, following intravenous administration to patients with advanced cancer," BMC Clinical Pharmacology, 11(1):1-8, 2011.

Lipp and Anklam, "Review of cocoa butter and alternative fats for use in chocolate-Part A. Compositional data," Food Chemistry, 62(1):73-97, 1998.

McPherson et al., "Enhancement of the activity of phenoxodiol by cisplatin in prostate cancer cells," British Journal of Cancer, 100(4):649-655, 2009.

Noxopharm Limited, "Phase Ia/Ib and Potential Phase IIa Study of the Safety and Pharmacokinetics of NOX66 Both as a Monotherapy and in Combination with Carboplatin in Patients with Refractory Solid Tumours," ClinicalTrials.gov archive [online] NCT02941523 on Oct. 20, 2016, retrieved from https://clinicaltrials.gov/archive/NCT02941523/2016_10 20, on May 2, 2017.

PCT International Search Report and Written Opinion issued in International Application No. PCT/AU2017/050300, dated May 24, 2017.

PCT International Search Report and Written Opinion issued in International Application No. PCT/AU2017/050363, dated May 25, 2017.

PCT International Search Report and Written Opinion issued in International Application No. PCT/AU2017/050301, dated May 25, 2017.

PCT International Search Report and Written Opinion issued in International Application No. PCT/AU2016/050674, dated Aug. 31, 2016.

Saif et al., "Flavonoids, phenoxodiol, and a novel agent, triphendiol, for the treatment of pancreaticobiliary cancers," Expert Opinion Investigational Drugs, 18(4):469-79, 2009.

Temozolomide prescription information, Feb. 2011 (Year: 2011).

Wang et al., "Prostate Cancer Treatment is Enhanced by Genistein In Vitro and In Vivo in a Syngeneic Orthotopic Tumor Model," Radiation Research, vol. 166, No. 1, Jul. 1, 2006 (Jul. 1, 2006), pp. 73-80, XP55626642, us ISSN: 0033-7587, DOI: 10.1667/RR3590.1.

Chakravarty et al., "Flt3L Therapy following Localized Tumor Irradiation Generates Long-Term Protective Immune Response in Metastatic Lung Cancer: Its Implication in Designing a Vaccination Strategy," *Oncology*, 70:245-254, 2006.

Liao et al., "Interleukin-2 at the Crossroads of Effector Responses, Tolerance, and Immunotherapy," *Immunity*, 38(1):13-25, 2013.

Yasuda et al., "Intratumoral injection of interleukin-2 augments the local and abscopal effects of radiotherapy in murine rectal cancer," *Cancer Sci.*, 102(7):1257-1263, 2011.

Ajazuddin et al., "Role of herbal bioactives as a potential bioavailability enhancer for Active Pharmaceutical Ingredients," *Fitoterapia*, 97:1-14, 2014.

Bandara et al., "Topical isoflavonoids reduce experimental cutaneous inflammation in mice," *Immunology and Cell Biology*, 88(7):727-733, 2010.

Block et al., "Immune System Effects of Echinacea, Ginseng, and Astragalus: A Review," *Integrative Cancer Therapies*, 2(3):247-267, 2003.

Burkard et al., "Dietary flavonoids and modulation of natural killer cells: implications in malignant and viral diseases," *Journal of Nutritional Biochemistry* 46:1-12, 2017.

Diomina, "Classification, nomenclature, and brief description of suppository bases," Development and Registration of Medicinal

(56) References Cited

OTHER PUBLICATIONS

Products, 2(15):1-10, 2016. (English abstract and English translation of Table 1 of Russian publication).

Fisher et al., "The effect of phospholipid structure on the thermal stability of rhodopsin," *Biochemica et Biophysica Acta*, 707(2):273-279, 1982.

Georgaki, et al., "Phenoxodiol, an anticancer isoflavene, induces immunomodulatory effects in vitro and in vivo," *Journal of Cellular and Molecular Medicine*, 13(9B):3929-3938, 2009.

Herst et al., "The antiproliferative effects of phenoxodiol are associated with inhibition of plasma membrane electron transport in tumour cell lines and primary immune cells," *Biochemical Pharmacology* 74:1587-1595, 2007.

Morré et al, "ECTO-NOX Target for the Anticancer Isoflavone Phenoxodiol," *Oncology Research*, 16:299-312, 2007.

Pinato et al., "Evolving concepts in the management of drug resistant ovarian cancer: Dose dense chemotherapy and the reversal of clinical platinum resistance," *Cancer Treat. Rev.*, http://dx.doi.org/10.1016/j.ctrv.2012.04.004. 8 pages. 2012.

Widyarini et al., "Isoflavonoid Compounds from Red Clover (Trifolium pratense) Protect from Inflammation and Immune Suppression Induced by UV Radiation," *Photochemistry and Photobiology*, 74(3):465-470, 2001.

"Idronoxil (Code C132257)," National Cancer Institute Thesaurus History, available online at https://ncit.nci.nih.gov/ncitbrowser/pages/concept_history.jsf?dictionary=NCI_Thesaurus&version=21.01d&code=C132257, accessed Mar. 4, 2021.

"Idronoxil (Code C2642)," National Cancer Institute Thesaurus History, available online at https://ncit.nci.nih.gov/ncitbrowser/pages/concept_history.jsf?dictionary=NCI_Thesaurus&version=21.01d&code=C2642, accessed Mar. 4, 2021.

Budman et al., "Identification of unique synergistic drug combinations associated with downexpression of surviving in a preclinical breast cancer model system," *Anticancer Drugs*, 23(2):272-279, 2012.

Choueiri et al., "Phase I trial of phenoxodiol delivered by continuous intravenous infusion in patients with solid cancer," *Annals of Oncology*, 17:860-865, 2006.

Kang et al., "Advances in drug delivery system for platinum agents based combination therapy," *Cancer Biol. Med.*, 12:362-374, 2015.

Park et al., "The effect of radiation on the immune response to cancer," *Int. J. Mol. Sci.*, 15:927-943, 2014.

Perez, "Carboplatin in combination therapy for metastatic cancer," *The Oncologist*, 9:518-52, 2004.

Tonekaboni et al., "Predictive approaches for drug combination discovery in cancer," *Briefings in Bioinformatics*, 19(2):262-276, 2018.

Nakaya et al., "Potential for immunotherapy combined with cytotoxic chemotherapy/radiotherapy," *Journal of Molecular Targeted Therapy for Cancer*, 13(4):24-28, 2015. (English translation of Japanese publication).

Suzuki et al., "Significance of radiation-induced bystander effects in radiation therapy," *Jpn. J. Med. Phys.*, 34(2):70-78, 2014. (English translation of Japanese publication).

\* cited by examiner

RADIOTHERAPY IMPROVEMENTS

This application is a national phase application under 35 U.S.C. § 371 of International Application No. PCT/AU2017/050299, filed Apr. 6, 2017, which claims the priority to U.S. Provisional Patent Application No. 62/318,946, filed Apr. 6, 2016, International Application No. PCT/AU2016/050674, filed Jul. 28, 2016, and to U.S. Provisional Patent Application No. 62/461,559, filed Feb. 21, 2017, the entirety of each are incorporated herein by reference.

FIELD OF THE INVENTION

The invention relates to radiotherapy of cancer and to abscopal responses to radiotherapy.

BACKGROUND OF THE INVENTION

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

Ionising radiation is a standard form of therapy in the management of cancer. Its objective is to induce damage to a cancer cell's DNA, RNA and cellular proteins to an extent that exceeds the ability of the cancer cell to repair that damage, leading to death of the cell.

When non-irradiated cells respond to radiation, the response is known as a "bystander effect". According to (Marin A. et al. 2015 *Reports Pract Oncol and Radiother* 20:12-21), a bystander effect may apply to cells which neighbour irradiated cells, or cells which do not neighbour irradiated cells. The latter includes cells that are located in non-irradiated tumours, and potentially tumours that are located in a different anatomical compartment to the tumour that has received radiation.

In general, the bystander effect observed in non-irradiated cells mimics the direct effects of radiation including an increased frequency of apoptosis, micro-nucleation, DNA strand breaks and mutations, altered levels or activity of regulatory proteins and enzymes, reduced clonogenic efficiency and oncogenic transformation.

Marin et al. supra describes the bystander effect applying to non-irradiated cells that neighbour irradiated cells as being "the radiobioloqical events arising from the radiation effect".

Where a bystander effect is observed in non-irradiated cells that are not neighbours of the irradiated cells, the effect is referred to as an 'abscopal effect', or an 'abscopal response' to irradiation and it has been explained as a "clinical change related to radiation effect".

In more detail, the result of radiotherapy at one tumour site may profoundly influence the biology of tumours at other locations in the body that have not been irradiated. Mole R et al 1953 *J Radiol* 26:234-41 described abscopal responses to radiotherapy some 70 years ago. Since this time, there have been numerous anecdotal reports of abscopal effects in patients receiving radiotherapy.

In one example, an abscopal response was observed in untreated metastatic disease following local primary tumour-directed therapy (Orton A. et al. 2016 *Cureus* 8(10): e821.DOI 10.7759/cureus.821). In another example, an abscopal response was observed in lung metastases of hepatocellular carcinoma (Okuma K et al. 2011 *J Med Case Rep* 5:111). Other examples include an abscopal effect in a case of toruliform para-aortic lymph node metastasis in a patient with advance uterine cervical carcinoma (Takava M et al 2007 *Anticancer Res;* 27-499-503) and in a patient treated with an anti-CTLA-4 antibody and radiotherapy for melanoma (Postow et al M 2012 *N Enql. J. Med* 366:925-31) and in hepatocellular carcinoma (Lock M et al. 2015 *Cureus* 7:e344, 10.7759/cureus.344). Other disease histologies where abscopal effects have been reported are described in Reynder K et al. 2015 *Cancer Treat Rev* 41:503-10.

Given the significant benefit to a patient of having all tumours within the body responding to the limited irradiation of a few tumours, it would be useful to increase the likelihood of formation of an abscopal effect in an individual having metastatic cancer, or even a condition involving a plurality of primary tumours, including benign tumours, as this would mean a higher likelihood that the irradiation of some of the individual's tumours might lead to a complete or partial response to radiotherapy, including for example the elimination or at least minimisation of some or all of the individual's non-irradiated tumours.

Further, treatment of tumours that are otherwise anatomically inaccessible to radiotherapy may also be possible.

Further, an abscopal response of tumours within the brain where the use of radiotherapy is highly restricted may be possible.

Prostate cancer is a disease of particular concern and that might benefit from an abscopal response, as this disease in metastatic form has a high mortality rate and sometimes presents in the form multiple metastatic nodules located in physiologically sensitive or anatomically inaccessible compartments such as the vertebrae.

As mentioned, abscopal responses to radiotherapy have generally been observed anecdotally. They are also infrequently reported.

Attempts to harness the effect, so as to reproducibly cause regression of non-irradiated tumours have utilised immunotherapy in combination with radiotherapy. While the CD-8 T cells and macrophages are considered by some to be an essential component of the effect in humans, the molecular basis for the effect, whether an immunological basis, or otherwise, remains unknown.

There is a need to improve the likelihood of formation of, or to induce the formation of, an abscopal effect to radiotherapy in an individual having multiple tumours, especially an individual having solid tumours, one example being metastatic prostate cancer.

There is a need to improve the likelihood of formation of, or to induce the formation of, a complete or partial response to radiotherapy in an individual wherein said individual has multiple tumours and in which some but not all of the tumours of the individual are irradiated, especially an individual having solid tumours, one example being metastatic prostate cancer.

SUMMARY OF THE INVENTION

The invention seeks to provide improvements in radiotherapy and/or to address one of the above mentioned needs and in one embodiment provides a method for inducing an abscopal response to radiotherapy in an individual including:
  providing an individual having a plurality of tumours,
  administering a compound of Formula I or Formula II to
    the individual, wherein Formula (I) is

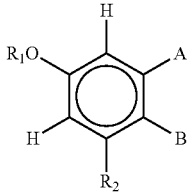

wherein
R₁ is H, or R$_A$CO where R$_A$ is $C_{1-10}$ alkyl or an amino acid;

R₂ is H, OH, or R$_B$ where R$_B$ is an amino acid or COR$_A$ where R$_A$ is as previously defined;

A and B together with the atoms between them form a six membered ring selected from the group

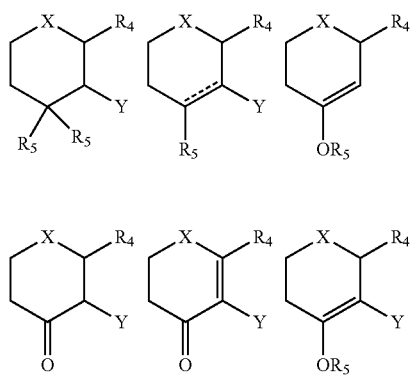

wherein
R₄ is H, COR$_D$ where R$_D$ is H, OH, $C_{1-10}$ alkyl or an amino acid, CO₂R$_C$ where R$_C$ is $C_{1-10}$ alkyl, COR$_E$ where R$_E$ is H, $C_{1-10}$ alkyl or an amino acid, or CONHR$_E$ where R$_E$ is as previously defined;

R₅ is H, CO₂R$_C$ where R$_C$ is as previously defined, or COR$_C$OR$_E$ where R$_C$ and R$_E$ are as previously defined, and where the two R₅ groups are attached to the same group they are the same or different;

X is O, N or S;

Y is

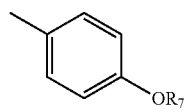

where R₇ is H, or $C_{1-10}$ alkyl; and

" ----- " represents either a single bond or a double bond; and wherein Formula II is:

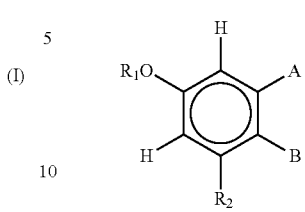

wherein
R₁ is H, or R$_A$CO where R$_A$ is $C_{1-10}$ alkyl or an amino acid;

R₂ is H, OH, or R$_B$ where R$_B$ is an amino acid or COR$_A$ where R$_A$ is as previously defined;

A and B together with the atoms between them form the group:

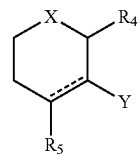

wherein
R₄ is H, COR$_D$ where R$_D$ is H, OH, $C_{1-10}$ alkyl or an amino acid, CO₂R$_C$ where R$_C$ is $C_{1-10}$ alkyl, COR$_E$ where R$_E$ is H, $C_{1-10}$ alkyl or an amino acid, or CONHR$_E$ where R$_E$ is as previously defined;

R₅ is substituted or unsubstituted aryl or substituted or unsubstituted heteroaryl;

X is O, N or S;

Y is

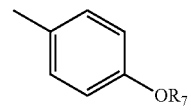

where R₇ is H, or $C_{1-10}$ alkyl; and

" ----- " represents either a single bond or a double bond,
  irradiating the individual with a cytotoxic dose of ionising radiation so that fewer than all of the plurality of tumours are irradiated, thereby resulting in the individual having irradiated and non-irradiated tumours, wherein one or more non-irradiated tumours regresses following the administration of the compound and the irradiation of the individual.

thereby inducing an abscopal response to radiotherapy in the individual.

In another embodiment there is provided a method for inducing a complete or partial response to radiotherapy in an individual wherein the individual has multiple tumours and the radiotherapy involves the irradiation of fewer than all of the tumours of the individual, including:
  providing an individual having multiple tumours,
  administering a compound of Formula I or Formula II (described above) to the individual,
  irradiating the individual with a cytotoxic dose of ionising radiation so that fewer than all of the tumours are irradiated, thereby resulting in the individual having irradiated and non-irradiated tumours, wherein one or more non-irradiated tumours regresses following the administration of the compound and the irradiation of the individual, thereby inducing a complete or partial response to radiotherapy in the individual.

In another embodiment there is provided a method for inducing a complete or partial response to radiotherapy in an individual wherein the individual has multiple tumours and the radiotherapy involves the irradiation of fewer than all of the tumours of the individual, including:

irradiating an individual having a plurality of tumours, and who has received a compound of Formula I or Formula II (described above), with a cytotoxic dose of ionising radiation so that fewer than all of the plurality of tumours are irradiated, thereby inducing a complete or partial response to radiotherapy in the individual.

In another embodiment there is provided a use of a compound of Formula I or Formula II (described above) for inducing a complete or partial response in an individual to radiotherapy of cancer wherein the individual has multiple tumours and the multiple tumours include irradiated tumours and at least one non-irradiated tumour.

In another embodiment there is provided a compound of Formula I or Formula II (described above) for use in inducing a complete or partial response in an individual to radiotherapy of cancer wherein the individual has multiple tumours and the multiple tumours include irradiated tumours and at least one non-irradiated tumour.

In the above described embodiments the tumours are typically solid tumours and may be prostate cancer, especially metastatic prostate cancer.

In the above described embodiments the compound of Formula I may be:

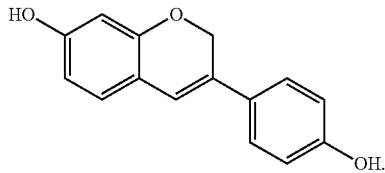 [SMILES: Oc1ccc(C2=Cc3ccc(O)cc3OC2)cc1]

In the above described embodiments the compound of Formula I, such as idronoxil, or of Formula II, may be administered rectally.

In another embodiment there is provided a kit for use in a method described above including:
a composition including a compound of Formula I or Formula II;
written instructions for use of the kit in a method for inducing an abscopal response to radiotherapy in an individual as described above.

Further aspects of the present invention and further embodiments of the aspects described in the preceding paragraphs will become apparent from the following description.

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

As described herein, the invention generally relates to improvements in radiotherapy that provide for abscopal responses in patients having multiple tumours. According to the invention, complete or partial responses of an individual to radiotherapy are observed in circumstances where some, but not all of the individual's tumours are irradiated, and especially in non-irradiated tumours that do not neighbour the irradiated tumours, for example tumours that are located outside of a field in which irradiation is given, examples of which include tumours that are located in the same organ or connective tissue but outside of the irradiation field, and tumours that are located in different organs, tissues or anatomical compartments to those tumours that are irradiated.

An 'irradiated tumour' refers to a tumour that has been exposed to a beam of ionising radiation for the purpose of causing regression of the tumour.

A 'non-irradiated tumours' refers to a tumour that (a) has not been exposed to a beam of ionising radiation and (b) that does not directly neighbour, or is not adjacent to an irradiated tumour.

The effect on non-irradiated tumours appears to derive from the irradiation of isoflavanoid-treated tumours. While not wanting to be bound by hypothesis it is believed that non-irradiated isoflavanoid treated tumours are susceptible to factors released from isoflavanoid treated irradiated tumours, resulting in the regression of non-irradiated tumours and observations of partial or complete responses. Further the abscopal effect leading to partial or complete response is not simply a function of radio-sensitisation of tumours to radiotherapy, because, by definition the effect is observed in non-irradiated tumours.

'Regression' and 'regress' and 'regresses' generally refers to the reduction in tumour size or growth of a tumour, resulting in the complete or partial involution or elimination of a tumour.

Thus in one embodiment there is provided a method for inducing a complete or partial response to radiotherapy in an individual or for inducing an abscopal response to radiotherapy wherein the individual has multiple tumours and the radiotherapy involves the irradiation of fewer than all of the tumours of the individual, including:

irradiating an individual having a plurality of tumours, and who has received a compound of Formula I or Formula II, with a cytotoxic dose of ionising radiation so that fewer than all of the plurality of tumours are irradiated, thereby inducing a complete or partial response to radiotherapy in the individual, or inducing an abscopal response to radiotherapy.

In another embodiment there is provided a method for inducing a complete or partial response to radiotherapy in an individual wherein the individual has multiple tumours and the radiotherapy involves the irradiation of fewer than all of the tumours of the individual, including:

providing an individual having multiple tumours, administering a compound of Formula I or Formula II to the individual, irradiating the individual with a cytotoxic dose of ionising radiation so that fewer than all of the tumours are irradiated, thereby resulting in the individual having irradiated and non-irradiated tumours, wherein one or more non-irradiated tumours regresses following the administration of the compound and the irradiation of the individual, thereby inducing a complete or partial response to radiotherapy in the individual.

A. Compounds

According to the invention, Compounds of Formula I or Formula II are utilised to provide improvements in radiotherapy and specifically to provide for regression of tumours that are not subjected to radiotherapy. These compounds are described by Formula I

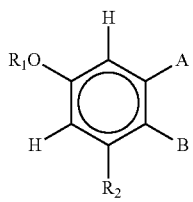

(I)

wherein $R_1$ is H, or $R_A CO$ where $R_A$ is $C_{1-10}$ alkyl or an amino acid;

$R_2$ is H, OH, or $R_B$ where $R_B$ is an amino acid or $COR_A$ where $R_A$ is as previously defined;

A and B together with the atoms between them form a six membered ring selected from the group

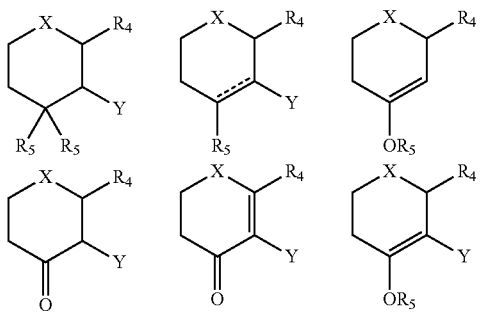

wherein $R_4$ is H, $COR_D$ where $R_D$ is H, OH, $C_{1-10}$ alkyl or an amino acid, $CO_2R_C$ where $R_C$ is $C_{1-10}$ alkyl, $COR_E$ where $R_E$ is H, $C_{1-10}$ alkyl or an amino acid, or $CONHR_E$ where $R_E$ is as previously defined;

$R_5$ is H, $CO_2R_C$ where $R_C$ is as previously defined, or $COR_C OR_E$ where $R_C$ and $R_E$ are as previously defined, and where the two $R_5$ groups are attached to the same group they are the same or different;

X is O, N or S;

Y is

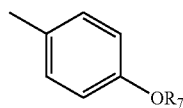

where $R_7$ is H, or $C_{1-10}$ alkyl; and

" ----- " represents either a single bond or a double bond.

Preferably, X is O.

In preferred embodiments, the compound of formula (I) is selected from the group consisting of

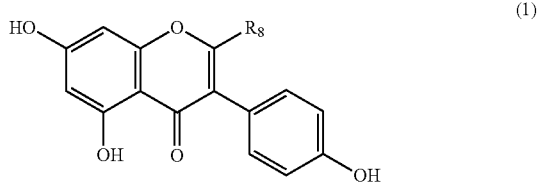

(1)

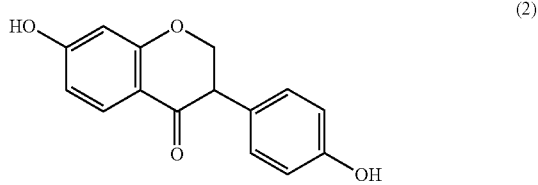

(2)

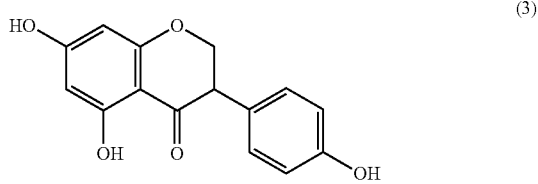

(3)

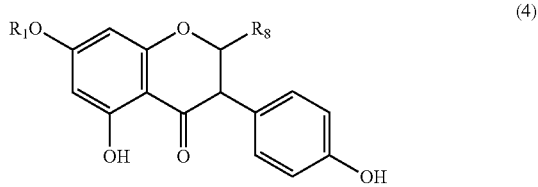

(4)

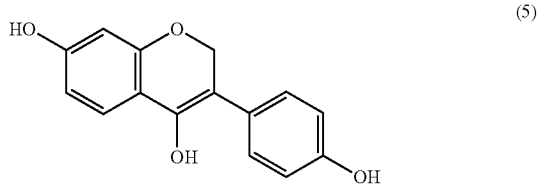

(5)

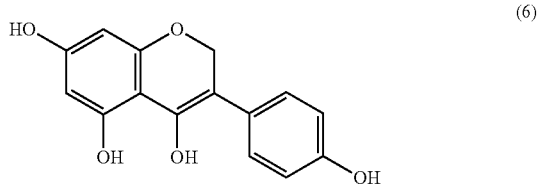

(6)

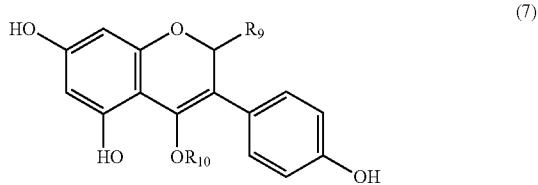

(7)

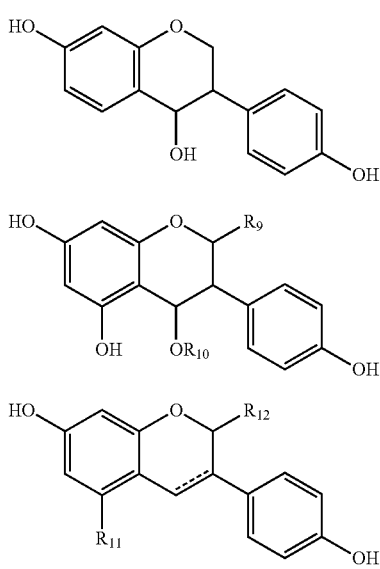

wherein
R₈ is H or $COR_D$ where $R_D$ is as previously defined;
R₉ is $CO_2R_C$ or $COR_E$ where $R_C$ and $R_E$ are as previously defined;
R₁₀ is $COR_C$ or $COR_COR_E$ where $R_C$ and $R_E$ are as previously defined; R₁₁ is H or OH;
R₁₂ is H, COOH, $CO_2R_C$ where $R_C$ and is as previously defined, or $CONHR_E$ where $R_E$ is as previously defined; and
" ----- " represents either a single bond or a double bond.

Some of the compounds discussed above may be referred to by the names dihydrodaidzein (compound 1 where R₈ is H), dihydrogenestein (compounds 2 and 5), tetrahydrodaidzein (compound 8) and equol and dehydroequol (compound 10).

Preferably, the compound of Formula (I) is

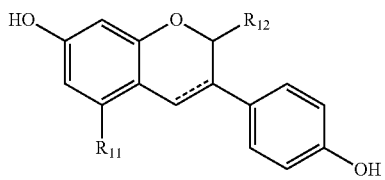

wherein R₁₁ and R₁₂ are as defined above.
Even more preferably, the compound of Formula (I) is

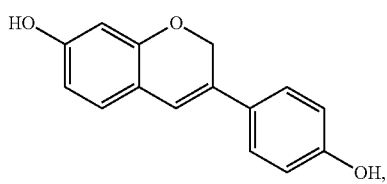

otherwise known as idronoxil (also known as phenoxodiol; dehydroequol; Haginin E (2H-1-Benzopyran-7-0,1,3-(4-hydroxyphenyl)).

In another aspect, the isoflavonoids for use in the methods of the invention described are shown by Formula II:

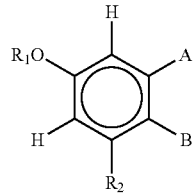

wherein
R₁ is H, or $R_ACO$ where $R_A$ is $C_{1-10}$ alkyl or an amino acid;
R₂ is H, OH, or $R_B$ where $R_B$ is an amino acid or $COR_A$ where $R_A$ is as previously defined;
A and B together with the atoms between them form the group:

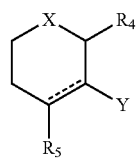

wherein
R₄ is H, $COR_D$ where $R_D$ is H, OH, $C_{1-10}$ alkyl or an amino acid, $CO_2R_C$ where $R_C$ is $C_{1-10}$ alkyl, $COR_E$ where $R_E$ is H, $C_{1-10}$ alkyl or an amino acid, or $CONHR_E$ where $R_E$ is as previously defined;
R₅ is substituted or unsubstituted aryl or substituted or unsubstituted heteroaryl;
X is O, N or S;
Y is

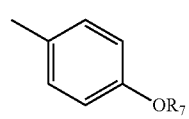

where R₇ is H, or $C_{1-10}$ alkyl; and
" ----- " represents either a single bond or a double bond.

In one preferred embodiment, R₅ is aryl substituted with an alkoxy group. Preferably, the alkoxy group is methoxy. In another preferred embodiment, R₅ is hydroxyl-substituted aryl.

In preferred embodiments, the compound of Formula II is

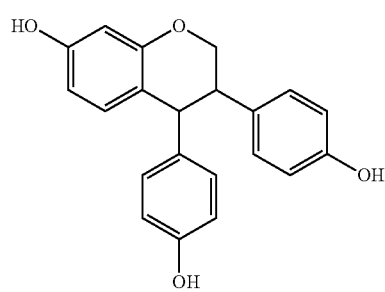

or

-continued

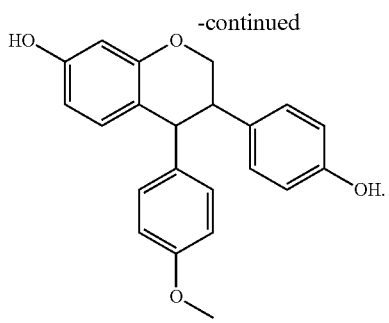

As used herein the term "alkyl" refers to a straight or branched chain hydrocarbon radical having from one to ten carbon atoms, or any range between, i.e. it contains 1, 2, 3, 4, 5, 6, 7, 8, 9 or 10 carbon atoms. The alkyl group is optionally substituted with substituents, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_{1-10}$ alkyl" refers to an alkyl group, as defined above, containing at least 1, and at most 10 carbon atoms respectively, or any range in between (e.g. alkyl groups containing 2-5 carbon atoms are also within the range of $C_{1-10}$).

Preferably the alkyl groups contain from 1 to 5 carbons and more preferably are methyl, ethyl or propyl.

As used herein, the term "aryl" refers to an optionally substituted benzene ring. The aryl group is optionally substituted with substituents, multiple degrees of substitution being allowed.

As used herein, the term "heteroaryl" refers to a monocyclic five, six or seven membered aromatic ring containing one or more nitrogen, sulfur, and/or oxygen heteroatoms, where N-oxides and sulfur oxides and dioxides are permissible heteroatom substitutions and may be optionally substituted with up to three members. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl and substituted versions thereof.

A "substituent" as used herein, refers to a molecular moiety that is covalently bonded to an atom within a molecule of interest. For example, a "ring substituent" may be a moiety such as a halogen, alkyl group, or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterised and tested for biological activity.

The terms "optionally substituted" or "may be substituted" and the like, as used throughout the specification, denotes that the group may or may not be further substituted, with one or more non-hydrogen substituent groups. Suitable chemically viable substituents for a particular functional group will be apparent to those skilled in the art.

Examples of substituents include but are not limited to: $C_1$-$C_6$ alkyl, $C_1$-$C_6$ haloalkyl, $C_1$-$C_6$ haloalkoxy, $C_1$-$C_6$ hydroxyalkyl, $C_3$-$C_7$ heterocyclyl, $C_3$-$C_7$ cycloalkyl, $C_1$-$C_6$ alkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino, acyl, carboxy, carbamoyl, aminosulfonyl, acyloxy, alkoxycarbonyl, nitro, cyano or halogen.

The term "isoflavonoid" as used herein is to be taken broadly and includes isoflavones, isoflavenes, isoflavans, isoflavanones, isoflavanols and similar or related compounds. Some non-limiting examples of isoflavonoid core structures are shown below:

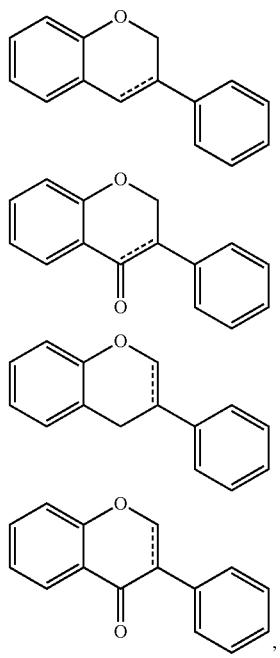

wherein " ===== " represents either a single bond or a double bond.

Methods for synthesis of the above described compounds are described in WO1998/008503 and WO2005/049008 and references cited therein towards the synthesis, the contents of which are incorporated herein by reference in entirety.

B. Dosage

Certain isoflavonoids according to Formula I and Formula II, and in particular, genestein and idronoxil have been proposed for use in treatment of cancer, especially metastatic disease involving solid tumours. However, in various clinical trials these compounds have been observed to be unable to provide either a complete or partial response to cancer, and at best they may slow disease progression. In particular, in a phase Ib/IIa safety and efficacy study of idronoxil in males with hormone refractory prostate cancer given idronoxil ranging from 20 to 400 mg, the disease had progressed in most individuals by 6 months from treatment Alvaro A. *US Oncological Review*, 2008; 4(1):39-41. Related observations were also made in clinical trials of idronoxil on other tumours, clearly pointing to the inability of the isoflavanoids alone, such as idronoxil alone, to provide a partial or complete response to treatment.

As described herein, the compounds of Formula I or II and especially idronoxil are provided to increase the likelihood of an abscopal response to radiotherapy. An 'abscopal response' is generally understood as referring to tumour regression at sites distant to an irradiated field, and is seen generally in patients with various types of metastatic tumours receiving palliative radiotherapy to a single metastasis. The tumour distant to the irradiated field that is susceptible to an abscopal effect may be located in the same anatomical compartment i.e. the same organ or connective tissue as the irradiated tumour.

A 'complete response' to therapy is generally understood as meaning the disappearance of all detectable signs of cancer in response to treatment. According to the invention, a complete response arises from the elimination of tumours by irradiation and the elimination of tumours (which are not irradiated) by the abscopal response or effect.

A 'partial response' is generally understood as meaning a decrease in tumour load in an individual, for example in terms of tumour number, size and growth rate. A partial response may increase the time to disease progression. According to the invention, a partial response may arise from the regression of tumours by irradiation and the regression of tumours (which are not irradiated) by the abscopal effect.

In the embodiments of the invention described herein, a clinical response, such as a complete response or a partial response may be defined by RECIST 1.0 criteria (Therasse P, et al.) 2000 *J. Natl Cancer Inst* 92:2015-16 as described in herein.

According to the invention a compound of Formula I or II is provided to the individual in amounts that at least increase the likelihood of formation of an abscopal response, or that at least increase the likelihood of creation of an abscopal effect as such a response or effect is important for providing either a partial or complete response in circumstances where some, but not all tumours of the individual are irradiated.

Typically a compound of Formula I or II, preferably idronoxil, is provided to the individual in amount of 10 to 30 mg/kg, preferably 15-25 mg/kg.

The compound of Formula I or II, preferably idronoxil, may be provided before the commencement of radiotherapy, for example, for a period of up to 14 days, preferably from 1 to 7 days. Preferably the compound is provided on a consecutive daily basis.

The compound of Formula I or II, preferably idronoxil, may be provided in a daily amount of about 100 to 900 mg, preferably 400 or 800 mg.

The compound of Formula I or II, preferably idronoxil, may be provided on each day that radiotherapy is given.

The compound of Formula I or II, preferably idronoxil, may be provided for a period of up to 3 months post the final radiotherapy treatment, preferably for about 14 days.

In one embodiment, idronoxil is dosed daily for 13 consecutive days (1 day before radiotherapy, on each day of radiotherapy (totaling 5 days) and on each day for 7 days following radiotherapy.

In certain embodiments, a compound of Formula I or Formula II, preferably idronoxil is administered to the individual by rectal administration.

As described herein, the inventor has found that oleaginous bases (i.e. hydrophobic or lipophilic bases) enable the therapeutic effect of an isoflavonoid, whereas hydrophilic bases, such as PEG, cyclodextrin and the like do not.

In the disclosure below, 'base' may refer to a substance commonly used as a carrier in a suppository, pessary or intra-urethral device.

Generally the base has a solvent power for the isoflavonoid enabling at least partial, preferably complete dissolution of the isoflavonoid in the base.

The base may be comprised of, or consist of an oil or fat.

In one embodiment the base includes saturated fatty acids in an amount of 50 to 65% w/w base. Stearic acid may be included in an amount of 25 to 40% w/w base. Palmitic acid may be included in an amount of 25 to 30% w/w base. Longer chain saturated fatty acids such as myristic, arachidic and lauric acid may be included in an amount of <2% w/w base.

In one embodiment the lipophilic suppository base contains fatty acids and wherein 50 to 100% of the fatty acids of the base are saturated fatty acids, preferably, 90 to 99% of the fatty acids of the base are saturated fatty acids. 30 to 60%, preferably about 40% of fatty acids of the base may be stearic acid. 20 to 30%, preferably about 25% of fatty acids of the base may be palmitic acid. 15 to 25%, preferably about 20% of fatty acids of the base may be lauric acid. 5 to 10%, preferably about 8% of fatty acids of the base may be myristic acid.

Further described herein, it has been found that oleaginous bases that are high in unsaturated fatty acids tend to be less advantageous in the invention. Typically, the oleaginous base includes unsaturated fatty acids in an amount of 35 to 50% w/w base. Monounsaturated fatty acid may be included in an amount of 30 to 45% w/w base. Oleic acid may be included in an amount of 30 to 40% w/w base. Polyunsaturated fatty acids such as linoleic and alpha linolenic acid may be included in an amount of 0 to 5% w/w base.

Theobroma oil (cocoa butter) has been a traditional base in a suppository because of: (a) its non-toxic and non-irritant nature, and (b) its low melting point, meaning that it readily dissolves at body temperature when placed within a bodily cavity, However, it is increasingly being replaced for a number of reasons. One reason is its variability in composition, a consequence of its natural origins; theobroma oil also is polymorphic, meaning it has the ability to exist in more than one crystal form. Another is that the formulated product needs to be kept refrigerated because of its low melting point, rendering it unsuitable in tropical regions. This has led to a number of substitute products offering a range of advantages over theobroma oil such as greater consistency, decreased potential for rancidity, and greater ability to tailor phase transitions (melting and solidification) to specific formulation, processing, and storage requirements.

Nevertheless, theobroma oil or a hydrogenated vegetable oil has been found to be a preferred embodiment of the invention.

The oleaginous base may comprise a predominance of (>45% w/w base) of saturated fatty acids. The oleaginous base may be a Theobroma oil (cocoa butter) or an oil fraction or derivative or synthetic version thereof (such as a hydrogenated vegetable oil) having a saturated fatty acid profile substantially the same as, or identical to the fatty acid profile of Theobroma oil.

Other examples of oils that may be used to provide or obtain fatty acids useful as bases include those obtainable from natural sources such as canola oil, palm oil, soya bean oil, vegetable oil, and castor oil. Oils derived from these sources may be fractionated to obtain oil fractions containing saturated fatty acids.

The base may be formed or derived from a hard fat, butter or tallow.

A base may comprise esterified or non-esterified fatty acid chains. The fatty acid chains may be in the form of mono, di and triglycerides, preferably comprising saturated fatty acid chains of C9-20 chain length.

A suppository base may be formed from synthetic oils or fats, examples including Fattibase, Wecobee, Witepesoll (Dynamit Nobel, Germany), Suppocire (Gatefosse, France, Hydrokote and Dehydag.

The proportion of the oleaginous suppository base in the final product is a function of the dosage of active pharmaceutical ingredient and the presence of other pharmaceutical or inert ingredient (if any) but may be provided by way of example in an amount of about 1 to 99% w/w formulation.

The isoflavonoid compositions may be prepared as follows. The isoflavonoid is contacted with a suppository base (as described above) in molten form in conditions enabling at least partial, preferably complete or substantially complete dissolution of the isoflavonoid in the base. This solution is then poured into a suitable mould, such as a PVC, polyethylene, or aluminium mould. For example, the isoflavonoid may be contacted with the base at a temperature of from about 35° C. to about 50° C. and preferably from about 40° C. to about 44° C. The isoflavonoid can be milled or sieved prior to contact with the base.

In one embodiment, the conditions provided for manufacture, and formulation or device formed from same, enable at least, or provide at least, 50%, preferably 60%, preferably 70%, preferably 80%, preferably 90%, preferably 95% of the isoflavonoid for a given dosage unit to be dissolved in the dosage unit. In these embodiments, no more than 50% of the isoflavonoid for a given dosage unit, preferably no more than 40%, preferably no more than 30%, preferably no more than 20%, preferably no more than 10%, preferably no more than 5% of isoflavonoid for a given dosage unit may be in admixture with, (i.e. undissolved in) the suppository base of the dosage unit.

In a preferred embodiment, all of the isoflavonoid added to a dosage unit is dissolved in the base. In this embodiment, no isoflavonoid is left in admixture with the suppository base. This is believed to increase the likelihood of the uptake of all of the isoflavonoid given in the dosage unit.

It will be understood that the objective of the manufacture process is not to admix, or to mingle, or to blend the suppository base with the isoflavonoid as generally occurs in pharmacy practice of admixing components, as it is believed that the resulting admixture would have a lower likelihood of providing therapeutic benefit. In this context, it is particularly important that any other excipient, carrier or other pharmaceutical active does not interfere with the dissolution of the isoflavonoid in the base, for example as may occur if the isoflavonoid forms a complex with a charged molecular species (other pharmaceutical active, carrier or excipient), the result of which would be to decrease the propensity of the complex, and therefore the isoflavonoid contained in it, to dissolve in the suppository base.

Optionally the suppositories, pessaries or intra-urethral devices may be coated, prior to packing, for example with cetyl alcohol, macrogol or polyvinyl alcohol and polysorbates to increase disintegration time or lubrication or to reduce adhesion on storage.

One or more sample suppositories, pessaries, or intra-urethral devices from each batch produced are preferably tested by the dissolution method of the present invention for quality control. According to a preferred embodiment, a sample from each batch is tested to determine whether at least about 75 or 80% by weight of the base dissolves within 2 hours.

Typically the suppository, pessary or like device according to the invention is substantially hydrophobic or lipophilic throughout and does not contain a hydrophilic substance such as hydrophilic carrier or pharmaceutical active, or hydrophilic foci or region formed from the ligation or complexing of the isoflavonoid to or with another pharmaceutical compound, carrier or excipient.

Preferably the formulation for forming the suppository, pessary and devices for urethral application does not include a further pharmaceutical active, cytotoxic or chemotherapeutic agent. In this embodiment, the only active is the isoflavonoid and the formulation does not include a platin, taxane or other cytotoxic or chemotherapeutic agent.

The total weight of the suppository preferably ranges from about 2250 to about 2700 mg and more preferably from about 2250 to about 2500 mg. According to one embodiment, the suppository has a total weight ranging from about 2300 mg to about 2500 mg.

The suppository or pessary is preferably smooth torpedo-shaped.

The melting point of the suppository or pessary is generally sufficient to melt in the patient's body, and is typically no more than about 37° C.

In one particularly preferred embodiment there is provided:
 a kit including:
  a plurality of suppositories sufficient in number to provide an individual with a suppository once daily, or twice daily, for a period of 30 to 90 days, preferably 30 to 60 days, preferably 30 days
  each suppository including:
   400 mg or 800 mg of idronoxil;
   a suppository base in the form of cocoa butter;
   wherein the suppository base in provided an amount of 1-99% w/w of the suppository,
  the kit further including:
   written instructions to provide the suppository once daily, or twice daily for a period of 30 to 90 days, preferably 30 to 60 days, preferably 30 days, preferably for use in a method described herein, preferably where the cancer is prostate cancer.

Methods for applying a suppository are well known in the art. Generally the methods involve inserting the suppository to a point aligned with the inferior and medial haemorrhoid veins, thereby enabling the release of the drug to the inferior vena cavea.

Methods for applying a pessary, or for urethral application of a pharmaceutically active ingredient are well known in the art.

C. Tumours

Embodiments of the invention described herein relate to the treatment of a range of solid tumours, enabling complete or partial response based on irradiation of certain tumours and abscopal responses in non-irradiated tumours.

The individual requiring treatment has at least two measurable tumours.

The tumours may include a primary tumour.

At least one of the tumours may be a metastatic or secondary tumour of a primary tumour. The secondary cancer may be located in any organ or tissue, and particularly those organs or tissues having relatively higher hemodynamic pressures, such as lung, liver, kidney, pancreas, bowel and brain.

Other examples of cancer include blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, leukemia or lymphoid malignancies, lung cancer including small-cell lung cancer (SGLG), non-small cell lung cancer (NSGLG), adenocarcinoma of the lung and squamous carcinoma of the lung, cancer of the peritoneum, hepatocellular cancer, gastric or stomach cancer including gastrointestinal cancer, pancreatic cancer, glioblastoma, ovarian cancer, liver cancer, bladder cancer, hepatoma, breast cancer (including metastatic breast cancer), colon cancer, rectal cancer, colorectal cancer, salivary gland carcinoma, kidney or renal cancer, prostate cancer, thyroid cancer, hepatic carcinoma, anal carcinoma, penile carcinoma, testicular cancer, oesophageal cancer, tumors of the biliary tract, as well as head and neck cancer.

In one particularly preferred embodiment, the cancer is primary or secondary prostate cancer, the isoflavonoid is idronoxil and the formulation is in the form of a suppository having a suppository base formed from, or consisting of Theobroma oil (cocoa butter). The idronoxil may be contained in the suppository in an amount of 400 mg or 800 mg. The idronoxil may be given once or twice daily for a period of 2 to 4 weeks, or for up to 12 months.

In one embodiment, the treatment provides for an inhibition of increase in prostate specific antigen (PSA) score, or for inhibition of tumour growth. In one embodiment the treatment provides for a reduction in PSA score, preferably a 50%, 60%, 70%, 80%, 90% or 100% reduction in PSA score.

D. Irradiation

As described herein, the invention includes the step of irradiating the individual requiring treatment with a cytotoxic dose of ionising radiation so that fewer than all of the tumours are irradiated, thereby resulting in the individual having irradiated and non-irradiated tumours.

Methods for the selective irradiation of tumours are very well known in the art. Methods such as stereotactic radiotherapy enable the precise focusing and delivery of an ionising beam of radiation to a particular anatomic or histologic region of tissue or organ and in particular enabling the irradiation of a tumour in one tissue or organ but not another tumour in the same tissue or organ.

Radiation therapy, radiotherapy, or radiation oncology is therapy using ionizing radiation, generally as part of cancer treatment to control or kill malignant cells. Radiation may be prescribed by a radiation oncologist for curative, adjuvant, neoadjuvant, therapeutic, or palliative treatment. It is also common to combine radiation therapy with surgery, chemotherapy, hormone therapy, immunotherapy or some mixture of the four. Most common cancer types can be treated with radiation therapy in some way. The precise treatment intent (curative, adjuvant, neoadjuvant, therapeutic, or palliative) will depend on the tumor type, location, and stage, as well as the general health of the patient. Total body irradiation (TBI) is a radiation therapy technique used to prepare the body to receive a bone marrow transplant. However, the disclosed methods generally involve the use of targeted, localized radiation therapy to promote an abscopal effect.

The amount of radiation used in photon radiation therapy is measured in gray (Gy), and varies depending on the type and stage of cancer being treated. For curative cases, the typical dose for a solid epithelial tumor ranges from 60 to 80 Gy, while lymphomas are treated with 20 to 40 Gy. Preventive (adjuvant) doses are typically around 45-60 Gy in 1.8-2 Gy fractions (for breast, head, and neck cancers.) Many other factors are considered by radiation oncologists when selecting a dose, including whether the patient is receiving chemotherapy, patient comorbidities, whether radiation therapy is being administered before or after surgery, and the degree of success of surgery.

Delivery parameters of a prescribed dose are determined during treatment planning (part of dosimetry). Treatment planning is generally performed on dedicated computers using specialized treatment planning software. Depending on the radiation delivery method, several angles or sources may be used to sum to the total necessary dose. The planner will try to design a plan that delivers a uniform prescription dose to the tumor and minimizes dose to surrounding healthy tissues.

The total dose is fractionated (spread out over time) for several important reasons.

Fractionation allows normal cells time to recover, while tumor cells are generally less efficient in repair between fractions. Fractionation also allows tumor cells that were in a relatively radioresistant phase of the cell cycle during one treatment to cycle into a sensitive phase of the cycle before the next fraction is given. Similarly, tumor cells that were chronically or acutely hypoxic (and therefore more radioresistant) may reoxygenate between fractions, improving the tumor cell kill.

In North America, Australia, and Europe, the standard fractionation schedule for adults is 1.8 to 2 Gy per day, five days a week. In some cancer types, prolongation of the fraction schedule over too long can allow for the tumor to begin repopulating, and for these tumor types, including head-and-neck and cervical squamous cell cancers, radiation treatment is preferably completed within a certain amount of time. For children, a typical fraction size may be 1.5 to 1.8 Gy per day, as smaller fraction sizes are associated with reduced incidence and severity of late-onset side effects in normal tissues.

In some cases, two fractions per day are used. This schedule, known as hyperfractionation, is used on tumors that regenerate more quickly when they are smaller. In particular, tumors in the head-and-neck demonstrate this behavior. One fractionation schedule that is increasingly being used and continues to be studied is hypofractionation. This is a radiation treatment in which the total dose of radiation is divided into large doses. Typical doses vary significantly by cancer type, from 2.2 Gy/fraction to 20 Gy/fraction. The logic behind hypofractionation is to lessen the possibility of the cancer returning by not giving the cells enough time to reproduce and also to exploit the unique biological radiation sensitivity of some tumors. One commonly treated site where there is very good evidence for such treatment is in breast cancer.

One of the best-known alternative fractionation schedules is Continuous Hyper-fractionated Accelerated Radiation therapy (CHART). CHART, used to treat lung cancer, consists of three smaller fractions per day. Although reasonably successful, CHART can be a strain on radiation therapy departments.

Another increasingly well-known alternative fractionation schedule, used to treat breast cancer, is called Accelerated Partial Breast Irradiation (APBI). APBI can be performed with either brachytherapy or with external beam radiation. APBI normally involves two high-dose fractions per day for five days, compared to whole breast irradiation, in which a single, smaller fraction is given five times a week over a six-to-seven-week period. An example of APBI where the entire dose is delivered in a single fraction is TARGIT.

The methods provided herein can be performed with any suitable radiotherapy, including, but not limited to, external beam radiotherapy, also known as teletherapy; sealed source radiotherapy, also known as brachytherapy; unsealed source radiotherapy; radioisotope therapy; and radioimmunotherapy.

In some embodiments, the radiotherapy is external radiation therapy. Examples of external radiation therapy include, but are not limited to, conventional external beam radiotherapy; three-dimensional conformal radiation therapy (3D-CR.T), which delivers shaped beams to closely fit the shape of a tumor from different directions; intensity modulated radiation therapy (IMRT), e.g., helical tomotherapy, which shapes the radiation beams to closely fit the shape of a tumor and also alters the radiation dose according to the shape of the tumor; conformal proton beam radiation therapy; image-guided radiotherapy (IGRT), which combines scanning and radiation technologies to provide real time images of a tumor to guide the radiation treatment; intraoperative radiation therapy (TORT), which delivers radiation directly to a tumor during surgery; stereotactic radiosurgery, which delivers a large, precise radiation dose to a small tumor area in a single session; hyperfractionated radiotherapy, e.g., continuous hyperfractionated accelerated radiotherapy (CHART), in which more than one treatment (fraction) of radiotherapy are given to a subject per day; and hypofractionated radiotherapy, in which larger doses of radiotherapy per fraction is given but fewer fractions.

In another embodiment, the radiotherapy is internal radiation therapy. Example of internal radiation therapy include, but are not limited to, interstitial, intracavitary, intraluminal, intravenously radiation therapy, and implant radiation therapy, such as implantation of radioactive beads, particles, or seeds. In some embodiments, the radiotherapy is sealed source radiotherapy. In another embodiment, the radiotherapy is unsealed source radiotherapy.

In yet another embodiment, the radiotherapy is radioisotope therapy or radioimmunotherapy, where the radiotherapy is performed by administering a radioisotope parenterally to a subject, e.g., by injecting to a subject a tumor-specific antibody-radioisotope conjugate. Suitable radioisotopes for radioisotope therapy or radioimmunotherapy include, but are not limited to, 72As, i98Au, 206Bi, 77Br, C, i4C, 47Ca, i29Ce, 137Ce, 55Co, 56Co, 57Co, 58Co, 60Co, 51Cr, 6iCu, 16 9Er/t8F, 52Fe, 55Fe, 59Fe, 67Ga, u % u % i % mln, i92 1r, 8i r, i 77Lu, 52Mg, I, 22Na, 24Na, 57NL 5 5 0, 32P, 203Pb, 103Pd,8 [Rb, 72Se, 7 Se, 75Se, [53Sm, 89Sr, 90Sr, T, "Tc, 201 Tl, i 67Tm, 90Y, 62Zn, and 13 Xe. Examples of reagents for radioisotope therapy and radioimmunotherapy include, but not limited to, metaiodobenzylguanidine, oral iodine-131, hormone-bound lutetium-177 and yttrium-90, ibritumomab tiuxetan, tositumomab iodine-131, radioactive glass or resins, and radioactive nanoparticles.

The choice of the radiation therapy can be determined by taking into consideration various factors, including, e.g., the type, size, and location of the tumor, the age, weight, and condition of the subject being treated. It is understood that the precise dose of the radiation and duration of treatment may vary with the age, weight, and condition of the subject being treated, and may be determined empirically using known testing protocols or by extrapolation from in vivo or in vitro test or diagnostic data. It is also understood that the total radiation dose required is often divided into two or more fractions, which are administered over an extended period of time. It is further understood that for any particular individual, specific dosage regimens could be adjusted over time according to the individual need and the professional judgment of the person administering or supervising the administration of the radiation.

In some embodiments, the total dose given in the radiotherapy is ranging from about 40 Gy to about 80 Gy. In certain embodiments, the total dose is divided into fractions and each fraction can be the same or different. Each fraction ranges from about 0.5 Gy to about 50 Gy.

In one embodiment the method includes the steps of:
assessing at least some of the tumours to determine at least one tumour for irradiation with the cytotoxic dose of ionising radiation; and
selecting at least one of the assessed tumours for irradiation with the cytotoxic dose of ionising radiation.

In one embodiment a tumour is assessed according to the size or diameter of the tumour.

In one embodiment the plurality of tumours is assessed according to the dose of radiotherapy required to provide cytoxicity to a tumour of the plurality of tumours.

In one embodiment a tumour is assessed according to anatomical location.

In one embodiment, a tumour selected for irradiation has a longest diameter of at least 10 mm.

In one embodiment, the one or more non-irradiated tumours are tumours that have a diameter of more than 10 mm.

In one embodiment, an irradiated tumour is located in or on the same organ, or in or on the same connective tissue as a non-irradiated tumour.

In one embodiment a primary tumour is irradiated, or a primary tumour and a metastatic tumour are irradiated.

In one embodiment a metastatic tumour is irradiated and a primary tumour is not irradiated.

D. Assessment of Treatment

The invention may include the further step of assessing one or more organs or tissues of an individual who has received the compound and irradiation, to determine the regression of a non-irradiated tumour in the individual. In one embodiment the step utilises radiological imaging to determine the location and volume for each of the plurality of tumor lesions in the subject after irradiation. For example, this can involve three-dimensional radiological images of the subject registering geographic locations of each of the plurality of tumor lesions. Non-limiting examples of radiological images that can be used to determine location and/or volume of a tumor lesion include positron emission tomography (PET) scans, x-ray computerized tomography (CT), magnetic resonance imaging (MRI), nuclear magnetic resonance imaging (NMRI), magnetic resonance tomography (MRT), or a combination thereof.

In one embodiment, all non-irradiated tumours regress.

In another embodiment, one or more non-irradiated tumours are eliminated.

In another embodiment, all non-irradiated tumours are eliminated.

In certain embodiments, the assessment of treatment follows the RECIST criteria as follows:
RECIST 1.0 Criteria
Definition of Measurable and Non-Measurable Disease
Measurable Disease:
The presence of at least one measurable lesion.
Measurable Lesion:
Lesions that can be accurately measured in at least one dimension, with the longest diameter (LD) being:
≥20 mm with conventional techniques (medical photograph [skin or oral lesion], palpation, plain X-ray, CT, or MRI),
OR
≥10 mm with spiral CT scan.

Non-measurable lesion: All other lesions including lesions too small to be considered measurable (longest diameter <20 mm with conventional techniques or <10 mm with spiral CT scan) including bone lesions, leptomeningeal disease, ascites, pleural or pericardial effusions, lymphangitis cutis/pulmonis, abdominal masses not confirmed and followed by imaging techniques, cystic lesions, or disease documented by indirect evidence only (e.g., by lab values).

Methods of Measurement

Conventional CT and MRI:

Minimum sized lesion should be twice the reconstruction interval. The minimum size of a baseline lesion may be 20 mm, provided the images are reconstructed contiguously at a minimum of 10 mm. MRI is preferred, and when used, lesions must be measured in the same anatomic plane by use of the same imaging sequences on subsequent examinations. Whenever possible, the same scanner should be used.

Spiral CT:

Minimum size of a baseline lesion may be 10 mm, provided the images are reconstructed contiguously at 5 mm intervals. This specification applies to the tumors of the chest, abdomen, and pelvis.

Chest X-Ray:

Lesions on chest X-ray are acceptable as measurable lesions when they are clearly defined and surrounded by aerated lung. However, MRI is preferable.

Clinical Examination:

Clinically detected lesions will only be considered measurable by RECIST criteria when they are superficial (e.g., skin nodules and palpable lymph nodes). In the case of skin lesions, documentation by color photography—including a ruler and patient study number in the field of view to estimate the size of the lesion—is required.

Baseline Documentation of Target and Non-Target Lesions

All measurable lesions up to a maximum of five lesions per organ and ten lesions in total, representative of all involved organs, should be identified as target lesions and recorded and measured at baseline.

Target lesions should be selected on the basis of their size (lesions with the LD) and their suitability for accurate repeated measurements (either clinically or by imaging techniques).

A sum of the LD for all target lesions will be calculated and reported as the baseline sum LD. The baseline sum LD will be used as a reference by which to characterize the objective tumor response.

All other lesions (or sites of disease) should be identified as non-target lesions and should also be recorded at baseline. Measurements of these lesions are not required, but the presence or absence of each should be noted throughout follow-up.

Documentation of indicator lesion(s) should include date of assessment, description of lesion site, dimensions, and type of diagnostic study used to follow lesion(s).

All measurements should be taken and recorded in metric notation, using a ruler or callipers.

Response Criteria

Disease assessments are to be performed every 6 weeks after initiating treatment. However, subjects experiencing a partial or complete response must have a confirmatory disease assessment at least 28 days later. Assessment should be performed as close to 28 days later (as scheduling allows), but no earlier than 28 days.

Definitions for assessment of response for target lesion(s) are as follows:

Evaluation of Target Lesions

Complete Response (CR)—disappearance of all target lesions.

Partial Response (PR)—at least a 30% decrease in the sum of the LD of target lesions, taking as a reference, the baseline sum LD.

Stable Disease (SD)—neither sufficient shrinkage to qualify for PR nor sufficient increase to qualify for progressive disease (PD), taking as a reference, the smallest sum LD since the treatment started. Lesions, taking as a reference, the smallest sum LD recorded since the treatment started or the appearance of one or more new lesions.

Evaluation of Non-Target Lesions

Definitions of the criteria used to determine the objective tumor response for non-target lesions are as follows:

Complete Response—the disappearance of all non-target lesions.

Incomplete Response/Stable Disease—the persistence of one or more non-target lesion(s).

Progressive Disease—the appearance of one or more new lesions and/or unequivocal progression of existing non-target lesions.

Evaluation of Overall Response for RECIST-Based Response

The overall response is the best response recorded from the start of the treatment until disease progression/recurrence is documented. In general, the subject's best response assignment will depend on the achievement of both measurement and confirmation criteria.

The following table presents the evaluation of best overall response for all possible combinations of tumor responses in target and non-target lesions with or without the appearance of new lesions.

| Target Lesion | Non-Target Lesion | New Lesion | Overall response |
|---|---|---|---|
| CR | CR | No | CR |
| CR | Incomplete response/(SD) | No | PR |
| PR | Non-PD | No | PR |
| SD | Non-PD | No | SD |
| PD | Any | Yes or No | PD |
| Any | PD | Yes of No | PD |
| Any | Any | Yes | PD |

Note:

Subjects with a global deterioration of health status requiring discontinuation of treatment without objective evidence of disease progression at that time should be classified as having "symptomatic deterioration". Every effort should be made to document the objective progression even after discontinuation of treatment.

In some circumstances, it may be difficult to distinguish residual disease from normal tissue. When the evaluation of complete response depends on this determination, it is recommended that the residual lesion be investigated (fine needle aspirate/biopsy) to confirm the complete response status.

Confirmation Criteria

To be assigned a status of PR or CR, a confirmatory disease assessment should be performed no less than 28 days after the criteria for response are first met.

To be assigned a status of SD, follow-up measurements must have met the SD criteria at least once after study entry at a minimum interval of 12 weeks.

E. Immunotherapy and Anti-Cancer Agents

In certain embodiments, the invention may include the administration of an immunotherapeutic agent (such as an antibody or cytokine) and/or the administration of a small molecule chemotherapeutic agent.

In some embodiments, the subject of the disclosed methods is further treated with an immunotherapy to enhance the abscopal effect. For example, dendritic cells (DCs) represent unique antigen-presenting cells capable of activating T cells to both new and recall antigens. In fact, these cells are the most potent antigen-presenting cells. The goal of DC based cancer immunotherapy is to use the cells to prime specific antitumor immunity through the generation of effector cells that attack and lyse tumors. Therefore, in some embodiments, the disclosed methods further involve administering DCs to the subject. In some embodiments, the DCs are administered directly to the tumor lesion site(s) being irradiated. In some embodiments, the DCs are administered systemically or to tumor site(s) in addition to or distinct from the sites being irradiated.

Additional immunotherapeutic approaches include 1) use of exogenous cytokines to non-specifically stimulate the immune system's effector cells to mount an anti-tumor response, 2) introduction of immuno-stimulatory antigens to precipitate a targeted immune response (i.e. active immunization or tumor vaccination), 3) exogenous expansion and reinfusion of tumor-specific immune cells (adoptive immunotherapy), 4) immune system checkpoint modulation, and 5) use of cancer-killing and immune system-stimulating modified viruses (oncolytic immunotherapy). Vaccination with telomerase vaccine (GV1001) can be combined with an immune adjuvant, e.g., granulocyte macrophage colony-stimulating factor (GM-CSF), and a cycle of gemcitabine chemotherapy.

Immunostimulatory cytokines include interferon alpha (IFN-α) and interleukin-2 (IL-2).

Anticancer vaccines can facilitate tumor antigen recognition and a subsequent anti-tumor immune response by artificially introducing tumor-associated antigens to the body, or cellular equipment that can help expose those already present. Artificially introduced antigens can take the form of peptide fragments, whole proteins, cell lysates or whole cells. For example, telomerase is highly expressed in essentially all cancer forms, while the expression in normal tissues is restricted. Moreover, telomerase activity is considered indispensable for tumor immortalization and growth. Human telomerase reverse transcriptase (hTERT), the rate-limiting subunit of the telomerase complex, is therefore an attractive target for cancer vaccination.

GV1001, a peptide vaccine representing a 16-aa hTERT sequence, binds multiple HLA class II molecules and harbors putative HLA class I epitopes. The peptide may therefore elicit combined CD4/CD8 T-cell responses, considered important to initiate tumor eradication and long-term memory.

Adoptive cell therapy (ACT) involves harvesting autologous lymphocytes from a patient's tumor or peripheral blood, expanding them and possibly modifying them in-vitro to express tumor-associated antigen receptors or secrete specific cytokines, and reintroducing them back into the host. The adoptive transfer of autologous tumor infiltrating lymphocytes (TIL) or in vitro re-directed peripheral blood mononuclear cells has been used to successfully treat patients with advanced solid tumors, including melanoma and colorectal carcinoma, as well as patients with CD19-expressing hematologic malignancies.

Immunomodulatory monoclonal antibody (mAb) therapies include cytotoxic T-Lymphocyte Antigen-4 (CTLA-4) inhibition (e.g., ipilimumab), Programmed Death-1 (PD-1) inhibition (e.g., nivolumab and pembrolizumab), CD40 agonism, OX40 agonism, Lymphocyte Activation Gene-3 (LAG-3) and T cell Immunoglobulin Mucin-3 (TIM-3) inhibition, and Tolllike receptor agonists. CTLA-4 is a T cell receptor that naturally interacts with B7-1 (CD-80) and B7-2 (CD-86) on the surface of antigen presenting cells, thereby down-regulating the T cell response and avoiding potential autoimmune damage. A costimulatory T cell surface protein, CD-28, on the other hand, competes with CTLA-4, albeit with less affinity, for interaction with B7-1 and B7-2, activating the T cell. Blocking CTLA-4 thereby allows CD-28 to interact with B7-1 and B7-2, enhancing the body's cellular immune response and ability to eradicate tumor cells. For poorly immunogenic tumors, CTLA-4 blockade may be effective if used in combination with vaccination with irradiated tumor cells modified to produce GM-CSF.

PD-1 receptor is expressed on B, T, and NK cells, and interacts with Programmed Death Ligands-1 and -2 (PDL-1 and -2), often subversively expressed on melanoma cells, to induce T cell exhaustion and down-regulate the immune response. By blocking PD-1, these medications facilitate a more vigorous anti-tumor cellular immune response. CD40 is a costimulatory receptor of the tumor necrosis factor (TNF) family normally expressed on a variety of cells including dendritic cells and macrophages. Interaction with its ligand plays a key role in priming and proliferation of antigen-specific CD4 T cells. When expressed on tumor cells, its stimulation results in apoptosis. Thus, CD40-stimulating mAbs (e.g., CD-870873) have direct anti-tumor activity and induce tumor antigen-specific T cell responses. LAG-3 is a transmembrane protein expressed on T regulatory (T reg) cells that binds MHC II, often expressed on melanoma cells, thereby enhancing T reg activity, negatively regulating the cellular immune response, and protecting melanoma cells from apoptosis. Blocking LAG-3 could thus help the body fight tumor cells on two fronts. Another class of immunomodulators act upon TLRs, a group of cell-surface receptors found on sentinel immune cells like dendritic cells and macrophages that naturally activate an innate immune response upon contact with characteristic pathogen-related antigens. Topical treatment of melanoma with Imiquimod (IMQ), a TLR-7 agonist, has been shown to facilitate 1) tumor infiltration with immune effector cells such as activated, cytotoxic plasmacytoid DCs, 2) a type I IFN response, 3) anti-angiogenic defenses, and in some cases result in complete tumor regression.

The blockade of TGF-β by anti-TGF-β antibody can synergistically enhance tumor vaccine efficacy, which is mediated by CD8+ T cells. For example, fresolimumab is an antibody capable of neutralizing all human isoforms of transforming growth factor beta (TGF) and has demonstrated anticancer activity.

Generating optimal "killer" CD8 T cell responses also requires T cell receptor activation plus co-stimulation, which can be provided through ligation of tumor necrosis factor receptor family members, including OX40 (CD134) and 4-IBB (CD137). OX40 is of particular interest as treatment with an activating (agonist) anti-OX40 mAb augments T cell differentiation and cytolytic function leading to enhanced anti-tumor immunity against a variety of tumors.

Numerous anti-cancer drugs are available for combination with the present method and compositions. The following is a non-exhaustive list of anti-cancer (anti-neoplastic) drugs that can be used in conjunction with irradiation:

Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; BisantreneHydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; GemcitabineHydrochloride; Gold Au 198; Hydroxyurea; Idarubicin Hydrochloride; Ifosfamide; Ilmofosine; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; ProcarbazineHydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

In one embodiment of the invention, the individual receives carboplatin and idronoxil.

In one embodiment of the invention, the individual receives granulocyte macrophage colony stimulating factor (GMCSF) and idronoxil.

In one embodiment of the invention, the individual receives granulocyte macrophage colony stimulating factor (GMCSF), idronoxil and carboplatin.

It will be understood that the invention disclosed and defined in this specification extends to all alternative combinations of two or more of the individual features mentioned. All of these different combinations constitute various alternative aspects of the invention.

EXAMPLES

Example 1

Individuals selected for treatment have late-stage, metastatic, solid (non-haematologic) cancer with no standard therapeutic alternatives other than palliative radiotherapy for pain or symptom relief. The individuals have a minimum of 3 measurable lesions that are amenable to radiotherapy (RT) and a projected minimum life expectancy of 12 weeks.

Idronoxil is self-administered at home as a rectal suppository. Individuals are instructed in the procedure of suppository administration.

Dosage is 400 mg daily (1×idronoxil containing suppository daily) for 7 consecutive days followed by 800 mg daily (1 idronoxil containing suppository twice daily) for 7 consecutive days.

One of 3 measurable lesions, or a maximum 2 of 4 or more measurable lesions will receive 25 Gy by external beam RT in 5 fractionated doses over 5 consecutive days. Multiple lesions are irradiated concurrently.

After a 14-day treatment cycle follow-up CT scans and clinical assessments are made 6- and 12-weeks post the completion of the treatment cycle.

Efficacy is assessed based on tumour response utilising CT scans and standard RECIST criteria and ECOG status. Tumour response is assessed by standard RECIST criteria; specifically, target lesions are the largest lesions (up to a maximum of 7 lesions) and are measured. Non-target lesions are all other lesions and are noted but not measured.

The invention claimed is:

1. A method for inducing an abscopal response to radiotherapy in an individual, including:
   irradiating an individual having a plurality of tumors, and who has received idronoxil, with a cytotoxic dose of ionising radiation so that fewer than all of the plurality of tumors are irradiated, thereby resulting in the individual having irradiated and non-irradiated tumors,
   wherein at least one of the tumors is a primary tumor, and at least one of the tumors is a metastatic or secondary tumor of a primary tumor;
   wherein at least one of the primary, or metastatic or secondary tumors, is a prostate tumor;
   wherein idronoxil is administered to the individual about 12 to 24 hours before irradiating the individual and,
   wherein idronoxil is administered for 13 consecutive days, including 1 day before radiotherapy, on each day of radiotherapy, wherein the individual receives radiotherapy in 5 fractionated doses over 5 consecutive days, and on each day for 7 days following radiotherapy;
   wherein one or more non-irradiated tumors regress following administration of idronoxil and the irradiation of the individual, thereby inducing an abscopal response to radiotherapy in the individual.

2. The method of claim 1, wherein idronoxil is administered to the individual by rectal administration.

3. The method of claim 1, wherein the one or more non-irradiated tumors are tumors that have a diameter of more than 10 mm.

4. The method of claim 1, wherein all non-irradiated tumors regress.

5. The method of claim 1, wherein one or more non-irradiated tumors are eliminated.

6. The method of claim 1, wherein all non-irradiated tumors are eliminated.

7. The method of claim 1, wherein an irradiated tumor is located in or on the same organ, or in or on the same connective tissue as a non-irradiated tumor.

8. The method of claim 1, including the steps of:
assessing at least some of the tumors to determine at least one tumor for irradiation with the cytotoxic dose of ionising radiation; and
selecting at least one of the assessed tumors for irradiation with the cytotoxic dose of ionising radiation.

9. The method of claim 8 wherein a tumor is assessed according to the size or diameter of the tumor.

10. The method according to claim 8 wherein the plurality of tumors is assessed according to the dose of radiotherapy required to provide cytotoxicity to a tumor of the plurality of tumors.

11. The method according to claim 8 wherein a tumor is assessed according to anatomical location.

12. The method according to claim 8 wherein the plurality of tumors are assessed according to the expression of one or more biomarkers.

13. The method of claim 8 wherein the tumor selected for irradiation has a longest diameter of at least 10 mm.

14. The method of claim 1, including the further step of:
assessing one or more organs or tissues of an individual who has received the compound and irradiation, to determine the regression of a non-irradiated tumor in the individual.

15. The method of claim 1, wherein the compound is administered to the individual in an amount of about 10 to 30 mg/kg.

16. The method of claim 1, wherein idronoxil is administered to the individual in a daily amount of about 100 to 900 mg.

17. The method of claim 1, wherein idronoxil is administered to the individual in a daily amount of about 400 or 800 mg.

18. The method of claim 1, wherein idronoxil is administered to the individual for a period of up to 14 days before the commencement of radiotherapy.

19. The method of claim 18, wherein idronoxil is administered to the individual for a period of 1 to 7 days before the commencement of radiotherapy.

20. The method of claim 1, wherein idronoxil is administered to the individual for a period of up to 3 months post the final radiotherapy treatment.

21. The method of claim 1, wherein idronoxil is administered to the individual for about 14 days post the final radiotherapy treatment.

* * * * *